United States Patent [19]

Srivastava

[11] Patent Number: 5,282,814
[45] Date of Patent: Feb. 1, 1994

[54] INSTRUMENT FOR CLEANING THE TOP OF THE HUMAN TONGUE WITH ANTISEPTIC STRIP

[76] Inventor: Rajesh Srivastava, 4921 Amanda Dr., Redding, Calif. 96002

[21] Appl. No.: 941,791

[22] Filed: Sep. 8, 1992

[51] Int. Cl.5 .............................................. A61B 17/24
[52] U.S. Cl. ................................................... 606/161
[58] Field of Search .......................... 30/346.5, 85, 41; 606/161

[56] References Cited

U.S. PATENT DOCUMENTS

| | | |
|---|---|---|
| D. 118,318 | 12/1939 | Fortunati . |
| D. 122,815 | 10/1940 | Crosby . |
| 194,364 | 8/1877 | Morgenthau . |
| D. 238,108 | 12/1975 | Cooke . |
| D. 253,789 | 12/1979 | Gupta .................. D24/23 |
| D. 265,506 | 7/1982 | Finamore . |
| D. 285,341 | 8/1986 | Audette . |
| D. 285,342 | 8/1986 | Audette . |
| D. 324,912 | 3/1992 | Hansen . |
| 697,336 | 4/1902 | Hagerty . |
| 963,630 | 7/1910 | McLean ................. 30/151 |
| 1,701,616 | 2/1929 | Gross . |
| 1,728,956 | 9/1929 | Darmitzel . |
| 1,811,775 | 6/1931 | Barkwill . |
| 1,860,924 | 5/1932 | Cooke . |
| 1,893,524 | 1/1933 | Shanley . |
| 3,254,356 | 6/1966 | Yao . |
| 3,602,277 | 8/1971 | Stump ................... 403/372 |
| 3,890,964 | 6/1975 | Castanado . |
| 4,455,704 | 1/1986 | Williams . |
| 4,488,327 | 12/1984 | Salder . |
| 4,582,059 | 4/1986 | Tiwari ................... 606/161 |
| 4,944,090 | 7/1990 | Sumnall ................. 30/41 |
| 5,005,246 | 4/1991 | Yon-Hui . |
| 5,027,511 | 7/1991 | Miller . |
| 5,095,619 | 3/1992 | Davis et al. ........... 30/41 |

FOREIGN PATENT DOCUMENTS 464169 4/1937 United Kingdom ............... 606/161

Primary Examiner—C. Fred Rosenbaum
Assistant Examiner—Noelle Kent Gring
Attorney, Agent, or Firm—Synnestvedt & Lechner

[57] ABSTRACT

An instrument for cleaning the top of the tongue comprises a blade held at an oblique angle to the top of the tongue and having a sharp, scraping edge at least along its bottom; it is of a width to fit easily within the mouth and to cover most of the width of the top of the tongue. Arm means, in the form of two forwardly-extending side arms or a single central arm are provided to enable the user to place the blade obliquely near the back of the tongue and pull it forwardly to scrape any coating or other debris from the top of the tongue. In various embodiments, the side portions of the blade may be curved forwardly to capture and pull forward materials scraped from the tongue, and optional antiseptic-laden strips may be adhered to one or both sides of the blade near one or both scraping edges to medicate the scraped area of the tongue.

2 Claims, 2 Drawing Sheets

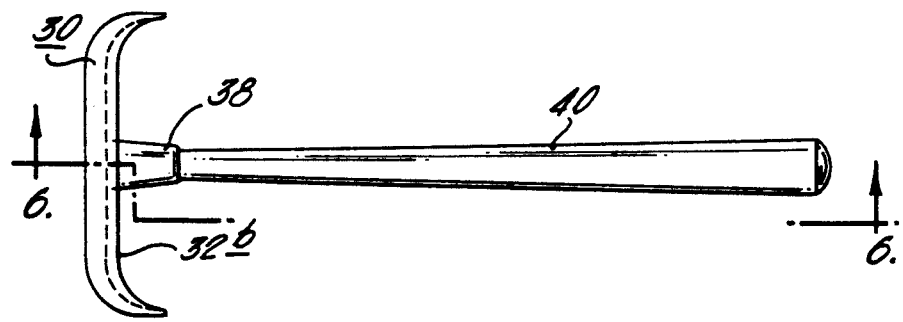
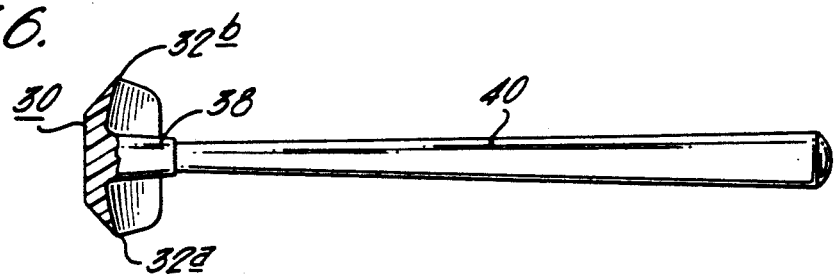
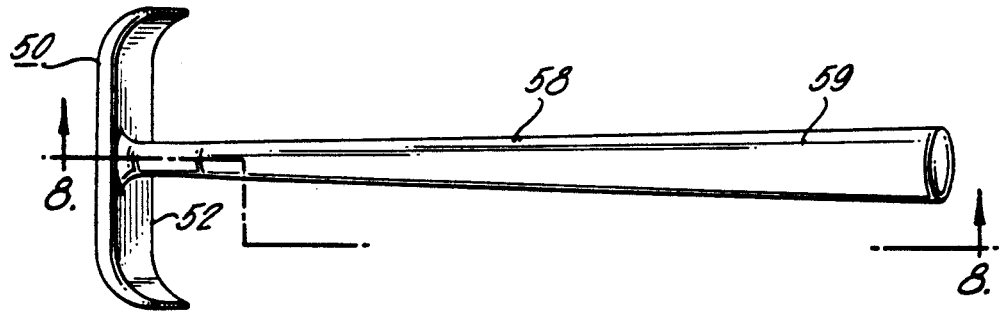
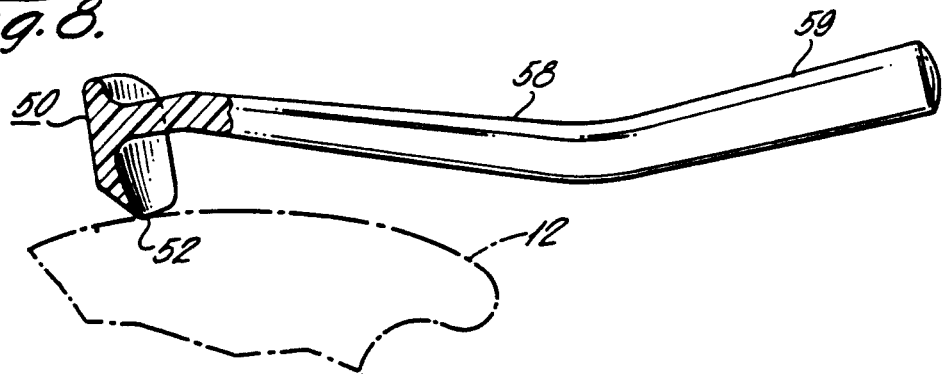

5,282,814

INSTRUMENT FOR CLEANING THE TOP OF THE HUMAN TONGUE WITH ANTISEPTIC STRIP

FIELD OF THE INVENTION

This invention relates to apparatus for cleaning the top surface of the human tongue, particularly to remove from it coatings of the type which are obnoxious, unhealthful and unaesthetic, and which contribute to halitosis.

BACKGROUND OF THE INVENTION

It is common for the human tongue to develop a coating which is unattractive and unhealthful, and which contributes to halitosis or bad breath. Although a dentist may sometimes recommend brushing the tongue with a toothbrush, this is generally found to be difficult, relatively ineffective and so unpleasant that people do not perform this hygiene on an appropriate regular basis. It is also especially difficult to clean the rearward portion of the tongue effectively in this manner.

It is an object of the present invention to provide an instrument for accomplishing the cleansing of a coating from the top surface of the human tongue, in a manner which is highly effective in cleaning the entire top surface of the tongue including its rearward portion, is easy to use, and is very inexpensive to make, as well.

SUMMARY OF THE INVENTION

According to the invention, there is provided an instrument for cleansing the top surface of the tongue which comprises a blade of a length to fit laterally in the human mouth across the top of the tongue, and which has a relatively sharp scraping edge along its bottom; arm means are secured to the blade which extend forwardly from the blade, whereby the arm means can be grasped in the fingers of a user to place the blade initially near the rear of the top of the tongue, and by which the blade can then be pulled forwardly along the top of the tongue with the blade angled downwardly so that its sharp edge plows along the top of the tongue and cleans it of coating materials.

In one preferred form, the arm means comprises a pair of arms at opposite sides of the blade, both of which are preferably used simultaneously in placing the blade into the mouth and in pulling it forward along the tongue. In another embodiment a single central handle is used. Scraping edges may be provided on one or both of the bottom and top of the blade, and in a preferred embodiment the blade is curved forwardly at both side edges to retain particles of coating removed by the scraping action.

In some embodiments it is also preferred to provide at least one antiseptic strip along the blade adjacent the scraping or ploughing edge, and preferably one on each side of each scraping edge thereby to apply mild medicament to the tongue during the scraping procedure.

To use the tongue cleaning device, the user merely grasps the arm means (the central arm in one embodiment, and the two side arms in another embodiment), uses these to lift the blade and place it in the back of the mouth on top of the rear of the tongue, and then pulls forwardly by the arm means so that the sharpened lower edge of the blade plows along the top surface of the tongue, scraping the coating off. This motion may be repeated several times if it appears that all of the coating is not removed in one stroke. The blade is then washed off and dried, and saved for the next occasion.

The blade is sharp enough to accomplish the desired removal of the coating without being so sharp as to present a damage of cutting the tongue. If the antiseptic strip is used, the antiseptic on the strip can be replaced or freshened upon each use, if desired, and by using a releasable adhesive to hold the strip in place, it can be replaced by a new strip when desired.

Other specific forms of the blade and pulling means may be utilized without departing from the spirit and scope of the invention.

BRIEF DESCRIPTION OF FIGURES

These and other objects and features of the invention will be more readily understood from a consideration of the following detailed description, taken with the accompanying drawings, in which:

FIG. 5 is a plan view of another embodiment of the tool of the invention;

FIG. 6 is a sectional elevational view taken on line 6—6 of FIG. 5;

FIG. 7 is a plan view of another embodiment of the invention; and

FIG. 8 is a sectional elevational view taken on line 8—8 of FIG. 7.

DESCRIPTION OF PREFERRED EMBODIMENTS

Figure 1:
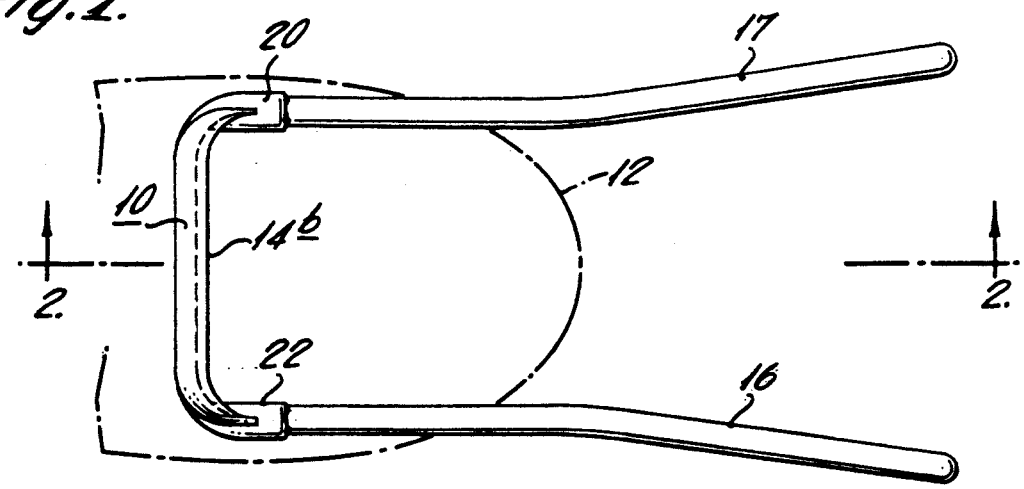
FIG. 1 is a plan view of a presently preferred embodiment of the invention, with the tongue shown in broken line.
Figure 2:
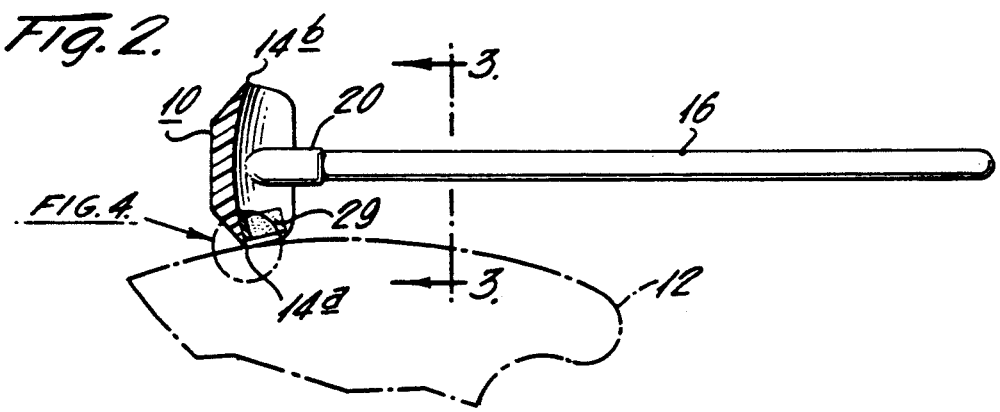
FIG. 2 is a sectional view taken on lines 2—2 of FIG. 1.
Figure 3:
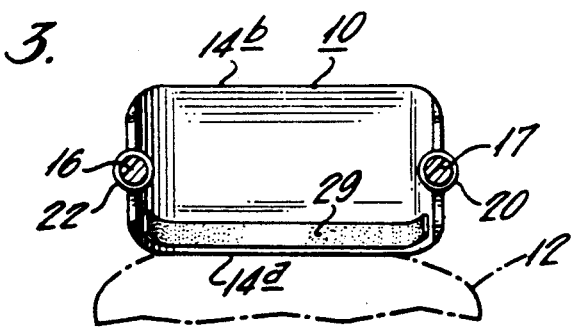
FIG. 3 is a sectional view, taken on line 3—3 of FIG. 2.

Referring now to the preferred embodiment of the invention shown in FIG. 1, it is seen to comprise a blade 10 having transverse dimensions such that it fits easily within the mouth and yet is long enough to extend substantially completely across the human tongue 12. Its lower edge 14a and its upper edge 14b are sharpened so as to enable them to provide a good scraping and plowing action without actually cutting the tongue; a pair of handles 16 and 17 extends forwardly from the blade at each end thereof, somewhat like the temple pieces of a pair of eyeglasses. The handles may be secured to the ends of the blade by forming the blade ends into tubes 20 and 22, into which the ends of the handles may be inserted and cemented.

Figure 4:
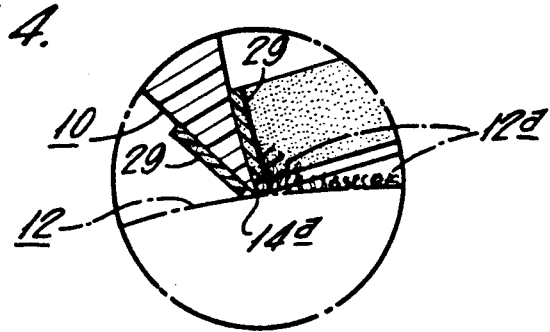
FIG. 4 is an enlarged fragmentary sectional view of the portion of the tool shown inside the broken-line circle in FIG. 2, but modified to show use of optional antiseptic strips on each side of the blade.

In use, one grasps the handles 16 and 17 in the fingers and uses them to lift and convey the blade 10 to a position near the rear of the tongue, the blade extending transversely across the tongue on the top side. By pulling forwardly on the arms 16 and 17, the blade is slid forwardly with its lower, sharpened edge plowing along the top surface of the tongue, to pick up and remove coating material, as shown in detail in FIG. 4 wherein 12a represents particles scraped from the tongue. One may use shorter strokes and/or longer strokes, depending upon how much coating material is to be removed and its distribution along the tongue. After the material is removed, one need only rinse one's mouth, rinse off the blade, dry it, and save it until the next occasion.

In this embodiment the blade is curved forwardly at its ends, the better to catch and entrap coating material dislodged by the scraping action. For the present purposes it is preferred that the blade be of a plastic material, and preferably the handles are of the same plastic material.

Because the pulling arms are at the sides, scraping can be accomplished more readily since the hands do not interfere with viewing the blade and the area being scraped.

Optionally employed are strips 29 of antiseptic-loaded absorbent material 29 extending along the blade parallel to and near its cutting edges. These may be secured by an appropriate releasable adhesive, and may be loaded with a mild antiseptic, particularly if the scraping action should happen to irritate the tongue surface. Similar strips may be used in any of the other embodiments of the invention.

FIGS. 5 and 6 show another embodiment of the invention in which a blade 30, sharpened along its lower and upper edges 32a and 32b and preferably made of plastic material, is provided with a single central arm 40. While it is possible to form this entire unit integrally by appropriate molding procedures, it is more economical to mold only the blade portion and to provide on the blade portion a central tubular extension 38 into which the central arm is cemented. Again, the ends of the blade are preferably curved forwardly to capture the tongue scrapings.

FIGS. 7 and 8 show a further embodiment of the invention, in which a scraping edge 52 is provided only along the bottom of the blade 50, and the portion 58 of the central handle near the blade is angled in a concave-upward configuration as a convenience in placing the blade in the desired positions on the tongue, while the portion 59 thereof is angled upwardly to permit easy operation at the desired angle.

In each of the embodiments shown, the rear side of the blade, i.e. the side away from the arm means, preferably makes an acute angle (see FIG. 4) with the adjacent top surface of the tongue; although some cleansing action can be obtained if the blade is normal to the tongue surface, or even at an obtuse angle, neither of the latter angles is preferred since they do not provide the true ploughing action desired for best cleaning.

Accordingly, there is provided an instrument which is very low in cost with respect to the materials used and the process for manufacturing it, but which is nevertheless very effective and simple to use.

While the invention has been shown and described with particular reference to specific embodiments in the interest of complete definiteness, it will be understood that it may be embodied in a variety of forms diverse from those specifically shown and described, without departing from the spirit and scope of the invention.

What is claimed is:

1. An instrument for cleaning the top surface of the human tongue, comprising:
   a blade of a length to fit comfortably in the human mouth in a position extending across the top of the tongue, and having a scraping edge at least along its bottom side;
   pulling arm means secured to said blade and extending forwardly therefrom, whereby said arm means can be grasped in the fingers of a user to place said blade initially near the rear of the top of the tongue and to pull it forwardly along the top of the tongue with said blade angled so that said edge scrapes the top of the tongue and cleanses it of coating materials; and
   a strip of antiseptic-loaded absorbent material secured to and along at least the rearward side of said edge without extending around said edge, to deliver antiseptic material to the tongue during the scraping procedure.

2. The instrument of claim 1, wherein said blade has only a single scraping edge and said arm means has a concave-upward shape along its length when said single scraping edge is turned downwardly.

* * * * *